(12) United States Patent
Irisawa

(10) Patent No.: US 9,351,646 B2
(45) Date of Patent: *May 31, 2016

(54) PHOTOACOUSTIC MEASUREMENT APPARATUS AND PROBE UNIT FOR USE THEREWITH, AND ENDOSCOPE

(71) Applicant: FUJIFILM Corporation, Tokyo (JP)

(72) Inventor: Kaku Irisawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 314 days.

This patent is subject to a terminal disclaimer.

(21) Appl. No.: 14/063,622

(22) Filed: Oct. 25, 2013

(65) Prior Publication Data

US 2014/0051967 A1 Feb. 20, 2014

Related U.S. Application Data

(63) Continuation of application No. PCT/JP2012/002770, filed on Apr. 23, 2012.

(30) Foreign Application Priority Data

Apr. 27, 2011 (JP) .................................. 2011-098969

(51) Int. Cl.
  *A61B 8/08* (2006.01)
  *A61B 5/00* (2006.01)
  *A61B 1/07* (2006.01)

(52) U.S. Cl.
  CPC .................. *A61B 5/0095* (2013.01); *A61B 1/07* (2013.01)

(58) Field of Classification Search
  CPC ...... A61B 5/0095; A61B 5/0093; A61B 8/08; A61B 5/7257; A61B 8/0825
  See application file for complete search history.

(56) References Cited

U.S. PATENT DOCUMENTS

| 8,879,352 B2* | 11/2014 | Witte .................. A61B 5/0093 367/7 |
| 9,131,851 B2* | 9/2015 | Fukutani .............. A61B 5/0091 |
| 2003/0187319 A1 | 10/2003 | Kaneko et al. |
| 2005/0004458 A1* | 1/2005 | Kanayama ........... A61B 5/0091 600/437 |
| 2014/0051967 A1* | 2/2014 | Irisawa ............... A61B 5/0095 600/407 |

FOREIGN PATENT DOCUMENTS

| CN | 100512760 | 7/2009 |
| JP | 2003-29126 A | 10/2003 |

(Continued)

OTHER PUBLICATIONS

Japanese Office Action dated Aug. 19, 2014 for Japanese Application No. 2011-098969 with English translation.

(Continued)

*Primary Examiner* — Joel Lamprecht
(74) *Attorney, Agent, or Firm* — Birch, Stewart, Kolasch & Birch, LLP

(57) ABSTRACT

A photoacoustic measurement apparatus which includes a diffuser plate which diffuses laser light inputted from the upstream side of an optical system, a lens system which focuses the laser light diffused by the diffuser plate, and an optical fiber cable which includes an optical fiber having a core and cladding structure and is disposed such that the laser light focused by the lens system is inputted from one end, in which the light projection unit projects the laser light guided by the optical fiber cable as the measuring light. In a photoacoustic measurement performed by guiding the measuring light using an optical fiber, high energy measuring light can be guided while inhibiting end face damage of the optical fiber.

18 Claims, 10 Drawing Sheets

(56) References Cited

FOREIGN PATENT DOCUMENTS

| JP | 2008-116209 A | 5/2008 |
| JP | 2010-12295 A | 1/2010 |

OTHER PUBLICATIONS

Chinese Office Action dated Nov. 3, 2014, for Chinese Application No. 201280020777.3 with English translation.

* cited by examiner

PHOTOACOUSTIC MEASUREMENT APPARATUS AND PROBE UNIT FOR USE THEREWITH, AND ENDOSCOPE

CROSS REFERENCE TO RELATED APPLICATIONS

This application is a Continuation of PCT International Application No. PCT/JP2012/002770 filed on Apr. 23, 2012, which claims the benefit to Patent Application No. 2011-098969 filed in Japan, on Apr. 27, 2011. The entire contents of all of the above applications are hereby incorporated by reference.

TECHNICAL FIELD

The present invention relates to a photoacoustic measurement apparatus for measuring a photoacoustic wave generated in a subject by the projection of light and probe unit used therewith. The invention also relates to an endoscope.

BACKGROUND ART

Conventionally, an ultrasonic imaging is known as a method for obtaining an internal tomographic image of a subject in which an ultrasonic image is generated by projecting an ultrasonic wave into a subject and detecting an ultrasonic wave reflected from the inside of the subject and a morphological tomographic image of the inside of the subject is obtained. In the mean time, the development of systems for displaying not only a morphological image but also a functional tomographic image has been in progress in recent years in the field of subject examination. As one of such systems, a system which uses photoacoustic spectroscopy is known. In the photoacoustic spectroscopy, light having a predetermined wavelength (e.g., visible light, near infrared light, or intermediate infrared light) is projected onto a subject and a photoacoustic wave which is an elastic wave generated in the subject as a result of absorption of the light energy by a particular substance is detected and the density of the particular substance is quantitatively measured (Japanese Unexamined Patent Publication No. 2010-012295). The particular substance in the subject is, for example, glucose or hemoglobin in the blood, or the like. The technology in which a photoacoustic wave is detected and a photoacoustic image is generated based on the detected signal in the manner described above is called photoacoustic imaging (PAI: Photoacoustic Imaging) or photoacoustic tomography (PAT: Photoacoustic Tomography).

Conventionally, the measurement which uses such photoacoustic effect (photoacoustic measurement) has the following problems. That is, the intensity of the light projected onto the subject is significantly attenuated while propagating inside of the subject by absorption and scattering. In addition, the intensity of photoacoustic wave generated inside of the subject based on the projected light is also attenuated while propagating inside of the subject by absorption and scattering. Consequently, it is difficult to obtain information of a deep portion of the subject by the photoacoustic measurement. In order to solve the problem, it is conceivable to enhance the photoacoustic wave to be generated by increasing the amount of energy of the light projected into a subject.

DISCLOSURE OF THE INVENTION

If measuring light having a high energy (not less than 1 mJ) required for the photoacoustic measurement is guided by an optical fiber, however, it is highly likely that the end face of the optical fiber is damaged, thereby posing a problem of durability of the optical fiber. When inputting the measuring light to an optical fiber, the end face of the optical fiber is normally placed at a position near the focal point of the lens such that the beam diameter of the measuring light fits within the core diameter of the optical fiber. But, when focused by the lens, the measuring light is focused too sharply and the energy is locally concentrated and the damage of the end face of the optical fiber progresses with the energy concentrated portion as the starting point. It is conceivable that the end face of the optical fiber is displaced from the near focal point position, but in this case, problems, such as local energy concentration and damage within the optical fiber, increase in energy coupling loss, and the like may possibly arise, so that a significant effect cannot be expected from this.

The present invention has been developed in view of the circumstances described above, and it is an object of the present invention to provide, in photoacoustic measurement performed by guiding the measuring light using an optical fiber, a photoacoustic measurement apparatus capable of guiding high energy measuring light while inhibiting end face damage of the optical fiber and a probe unit for use with the apparatus, and an endoscope.

In order to solve the problem described above, the photoacoustic measurement apparatus of the present invention includes:

a diffuser plate which diffuses measuring light inputted from the upstream side of an optical system;

a lens system which focuses the measuring light diffused by the diffuser plate;

an optical fiber cable which includes an optical fiber having a core and cladding structure and is disposed such that the measuring light focused by the lens system is inputted from one end;

a light projection unit which projects the measuring light guided by the optical fiber cable into a subject;

an electroacoustic transducer unit which detects a photoacoustic wave generated in the subject by the projection of the measuring light and converts the photoacoustic wave into an electrical signal; and a signal measurement unit which performs a signal measurement based on the electrical signal.

In the photoacoustic measurement apparatus according to the present invention, the lens system focuses the measuring light such that a minimum beam diameter of the measuring light is ⅓ to ⅔ of a core diameter of the optical fiber and the optical fiber cable is disposed such that the measuring light is inputted with a beam diameter of the measuring light being ⅓ to ⅔ of the core diameter of the optical fiber.

In the photoacoustic measurement apparatus according to the present invention, a divergence angle φ of the measuring light incident on the diffuser plate, a diffusion angle θ of the diffuser plate, a focal length f of the lens system, and a core diameter d of the optical fiber preferably satisfy a formula (1) given below.

$$\frac{d}{3} \le 2.4 \cdot f \cdot \tan\left(\sqrt{\left(\frac{\phi}{2}\right)^2 + \left(\frac{\theta}{2}\right)^2}\right) \le \frac{2d}{3} \quad (1)$$

The term "divergence angle" as used herein refers to a diverging angle of the beam diameter of the measuring light along with the propagation. The term "diffusion angle" of the diffuser plate as used herein refers to a diverging angle of the beam diameter of the measuring light along with the propagation when passed through the diffuser plate. The "divergence angle" and the "diffusion angle" as used herein are represented by a total plane angle. The term "beam diameter" as used herein refers to the $1/e^2$ diameter in which about 86.5% of the measuring light energy is included. When measuring these angles, it is preferable that the measurement is performed within the range in which the beam diameter is diffused from a certain beam diameter to 1.5 times the certain beam diameter.

In the photoacoustic measurement apparatus according to the present invention, it is preferable that the lens system has a focal length of 4 to 40 mm.

In the photoacoustic measurement apparatus according to the present invention, it is preferable that the diffuser plate is a holographic diffuser or a light shaping diffuser in which tiny concave lenses are arranged randomly on one surface of a substrate, and has a diffusion angle of 0.2 to 2.0°.

In the photoacoustic measurement apparatus according to the present invention, it is preferable that the optical fiber has a core diameter of 100 to 600 μm.

Preferably, the photoacoustic measurement apparatus according to the present invention includes a holding section which integrally holds the lens system and the optical fiber cable.

In the photoacoustic measurement apparatus according to the present invention, it is preferable that the holding section also integrally holds the diffuser plate.

Preferably, the photoacoustic measurement apparatus according to the present invention includes a branch section which branches the measuring light, and the diffuser plate, the lens system, and the optical fiber cable are disposed with respect to each optical path of the branched measuring light portions.

Alternatively, it is preferable that the photoacoustic measurement apparatus according to the present invention includes a branch section which branches the measuring light, and the diffuser plate is the sole diffuser plate provided and disposed so as to diffuse at least two of the branched measuring light portions, and the lens system and the optical fiber cable are disposed with respect to each optical path of the branched measuring light portions.

In the photoacoustic measurement apparatus according to the present invention, it is preferable that the lens system is a lens array, the optical fiber cable is provided in plural, and each end face of the plurality of optical fibers of the plurality of optical fiber cables on the lens array side is arranged so as to correspond to each lens section constituting the lens array.

In the photoacoustic measurement apparatus according to the present invention, it is preferable that the lens system is a micro-lens array, the optical fiber cable is a bundle fiber cable which includes a plurality of optical fibers, and each end face of the plurality of optical fibers of the bundle fiber cable on the micro-lens array side is arranged so as to correspond to each micro-lens constituting the micro-lens array.

The term "each end face of the plurality of optical fibers of the plurality of optical fiber cables (or bundle fiber cable, the same applies hereinafter in this paragraph) is arranged so as to correspond to each lens section (or micro-lens, the same applies hereinafter in this paragraph) constituting the lens array (or micro-lens array, the same applies hereinafter in this paragraph) refers to that the arrangement pattern of the end faces of the plurality of optical fibers substantially matches the focusing pattern of the lens array. The term that two patterns "substantially match" as used herein refers to that even when the these patterns are slightly different from each other, if the difference is within the range in which each of a plurality of portions of measuring light focused by each lens section constituting the lens array may be incident on each core of the plurality of optical fibers, the two patterns are deemed as matched. The term "arrangement pattern" of end faces as used herein refers to an arrangement pattern of representative points (e.g., core centers) of end faces of a plurality of optical fibers on one side. The term "focusing pattern" as used herein refers to a bright spot pattern formed on a focusing surface perpendicular to the optical axis of the lens array by a plurality of portions of the measuring light transmitted through each lens section constituting the lens array and focused.

Further, in the photoacoustic measurement apparatus according to the present invention, the measuring light may be light in a near infrared wavelength range, and the diffuser plate, the lens system, and the optical fiber cable may be of a structure capable of guiding light in the near infrared wavelength range.

Further, in the photoacoustic measurement apparatus according to the present invention, the signal measurement unit may be of a configuration which includes an acoustic image generation unit which generates a photoacoustic image with respect to the electrical signal of the photoacoustic wave. In this case, it is preferable that the electroacoustic transducer unit is configured to detect a reflected ultrasonic wave of an ultrasonic wave transmitted to the subject, and the acoustic image generation unit is configured to generate an ultrasonic image based on an ultrasonic wave signal of the reflected ultrasonic wave.

The probe unit according to the present invention is a probe unit for use with a photoacoustic measurement apparatus, including:

a diffuser plate which diffuses measuring light inputted from the upstream side of an optical system;

a lens system which focuses the measuring light diffused by the diffuser plate;

an optical fiber cable which includes an optical fiber having a core and cladding structure and is disposed such that the measuring light focused by the lens system is inputted from one end;

a light projection unit which projects the measuring light guided by the optical fiber cable into a subject;

an electroacoustic transducer unit which detects a photoacoustic wave generated in the subject by the projection of the measuring light and converts the photoacoustic wave into an electrical signal; and a signal measurement unit which performs a signal measurement based on the electrical signal.

The endoscope of the present invention includes the probe unit described above.

In a photoacoustic measurement apparatus equipped with a light projection unit which projects measuring light into a subject, an electroacoustic transducer unit which detects a photoacoustic wave generated in the subject by the projection of the measuring light and converts the photoacoustic wave into an electrical signal, and a signal measurement unit which performs a signal measurement based on the electrical signal, the photoacoustic measurement apparatus and the probe unit for use therewith, and endoscope according to the present invention includes a diffuser plate which diffuses the measuring light inputted from the upstream side of an optical system, a lens system which focuses the measuring light diffused by the diffuser plate, and an optical fiber cable which includes an optical fiber having a core and cladding structure and is disposed such that the measuring light focused by the lens system is inputted from one end, in which the light projection unit projects the measuring light guided by the optical fiber cable. That is, the distribution of propagation angles of luminous fluxes included in the measuring light is extended by passing the measuring light through the diffuser plate once, and the beam diameter when inputted to the optical fiber is controlled by the focal length of the lens system. This may prevent the measuring light from being focused too sharply when focused by the lens system and inputted to the optical fiber. This may prevent core damage at an optical fiber end face due to local energy exceeding the core damage threshold energy. As a result, in the photoacoustic measurement performed by guiding the measuring light using an optical fiber, high energy measuring light may be guided while inhibiting end face damage of the optical fiber.

BEST MODE FOR CARRYING OUT THE INVENTION

Figure 1:
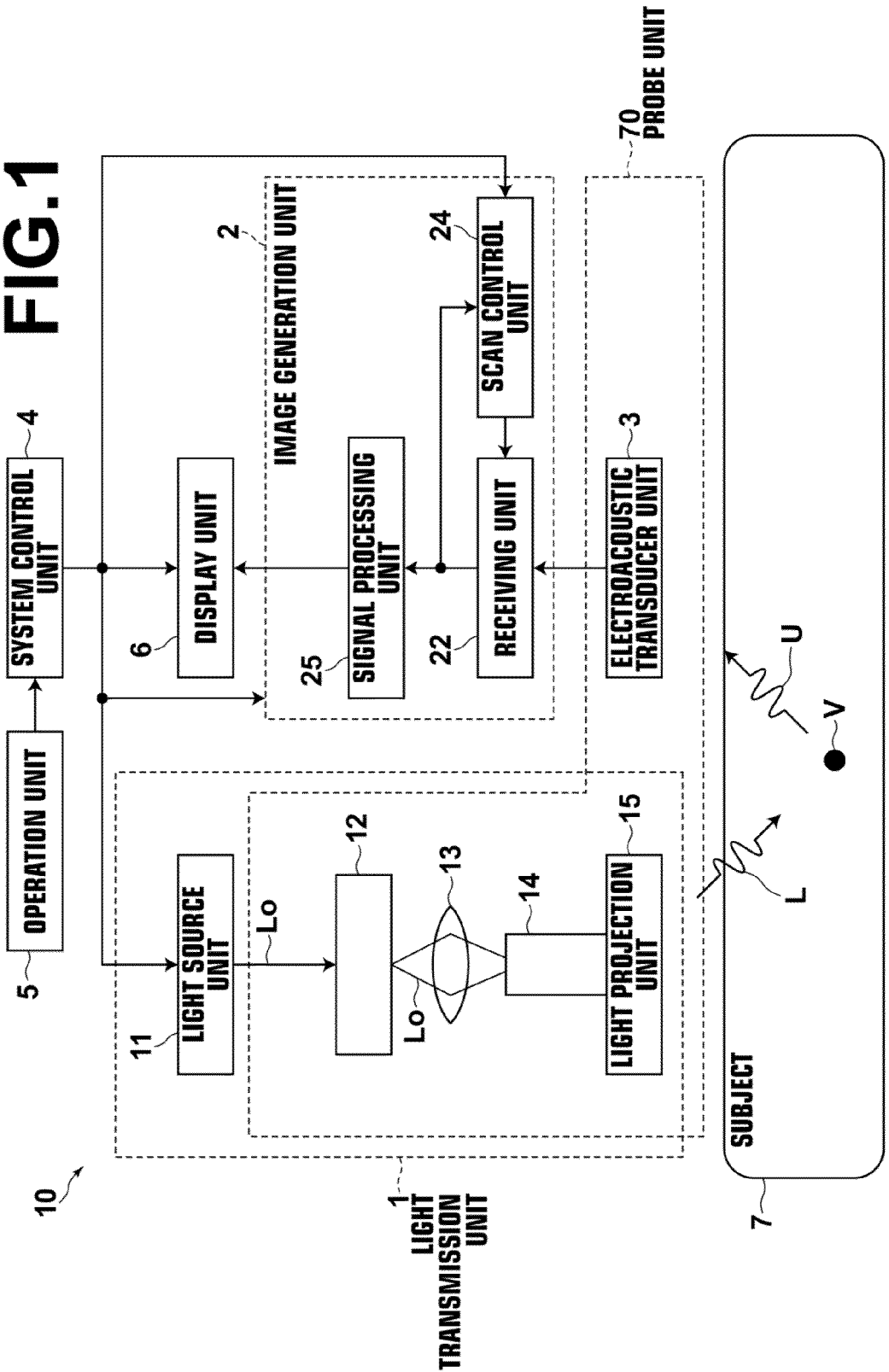
FIG. 1 is a schematic view of a photoacoustic imaging apparatus according to an embodiment, illustrating a configuration thereof.

Hereinafter, embodiments of the present invention will be described with reference to the accompanying drawings, but it should be appreciated that the present invention is not limited to these embodiments. Note that each component in the drawings is not necessarily drawn to scale in order to facilitate visual recognition.

[Embodiments of Photoacoustic Measurement Apparatus and Probe Unit Used Therewith, and Endoscope]

Figure 2:
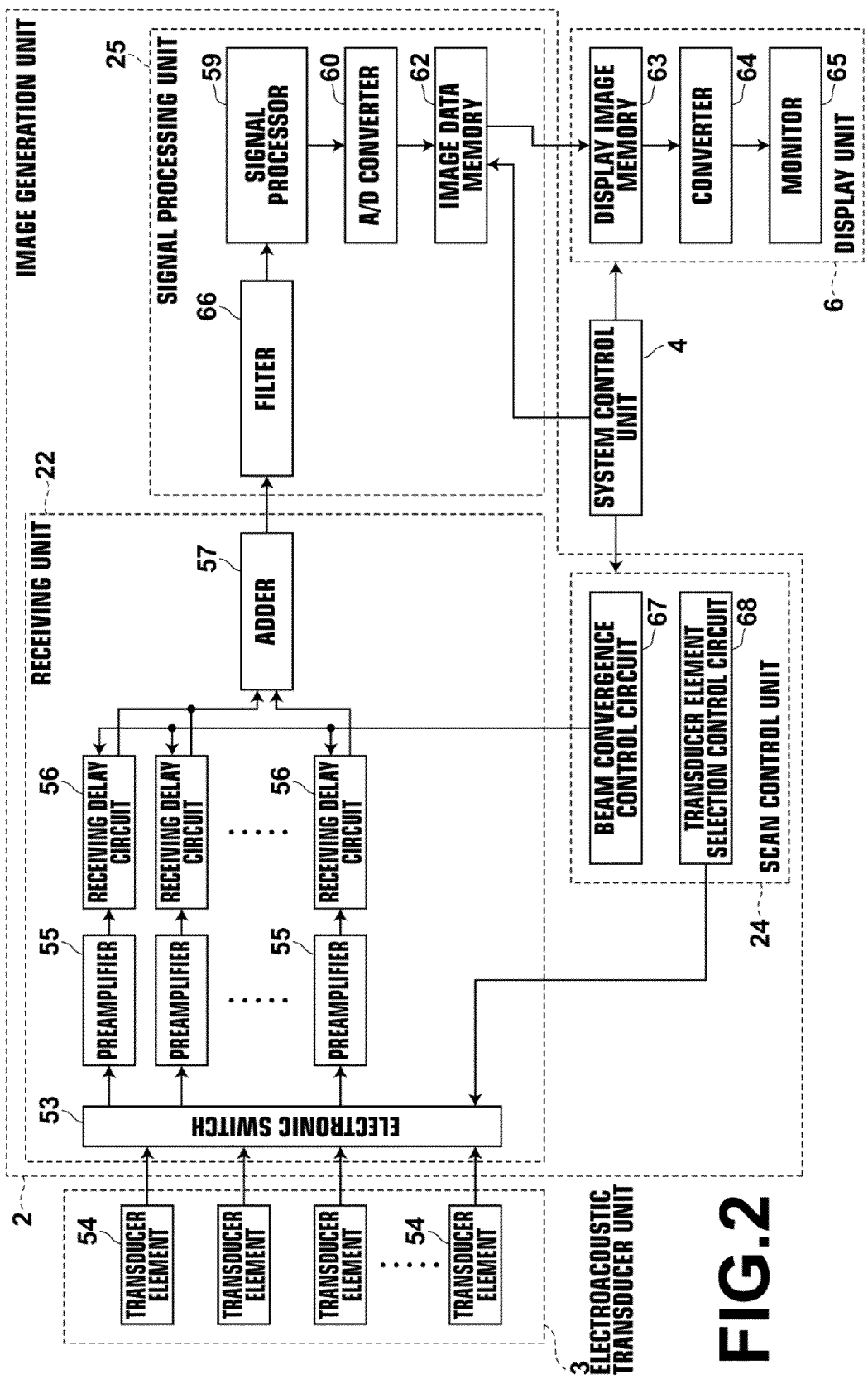
FIG. 2 is a block diagram of the image generation unit in FIG. 1, illustrating a configuration thereof.
Figure 3:
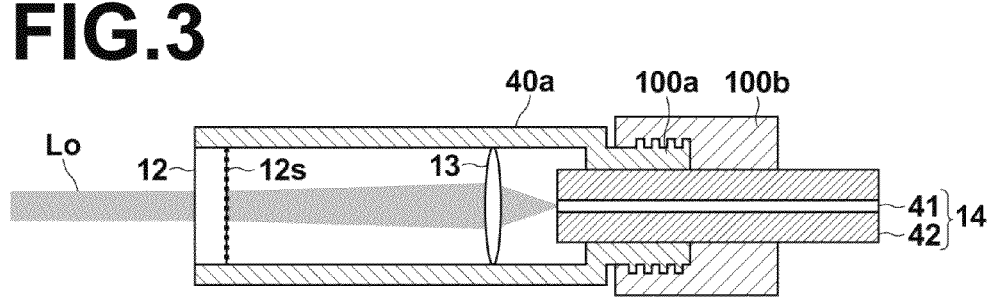
FIG. 3 is a schematic cross-sectional view of an embodiment of an optical system formed of a diffuser plate, a lens system, and an optical fiber cable, illustrating a configuration thereof.
Figure 4:
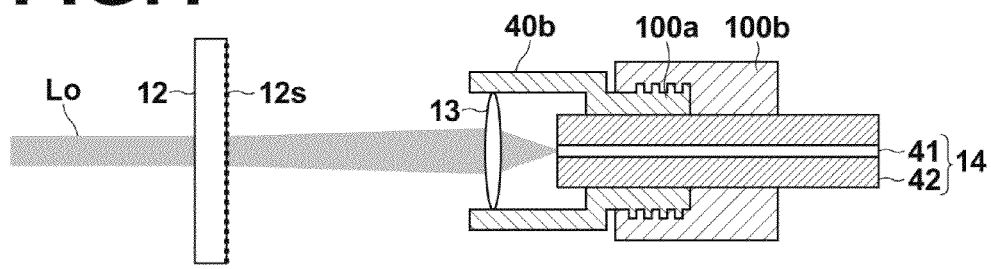
FIG. 4 is a schematic cross-sectional view of an embodiment of an optical system formed of a diffuser plate, a lens system, and an optical fiber cable, illustrating another configuration thereof.

An embodiment of the photoacoustic measurement apparatus of the present invention will be described. In the present embodiment, a specific description will be made of a case in which the photoacoustic measurement apparatus is a photoacoustic imaging apparatus which generates a photoacoustic image based on a photoacoustic signal. FIG. 1 is a schematic view of a photoacoustic imaging apparatus 10, illustrating an overall configuration thereof. FIG. 2 is a block diagram of the image generation unit 2 in FIG. 1, illustrating a configuration thereof. FIGS. 3 and 4 are schematic cross-section views of embodiments of an optical system of the present invention formed of a diffuser plate 12, a lens system 13, and an optical fiber cable 14, illustrating configurations thereof.

The photoacoustic imaging apparatus 10 according to the present embodiment includes a light transmission unit 1 which generates measuring light L which includes a particular wavelength component and projects the measuring light L onto a subject 7, an image generation unit 2 which detects a photoacoustic wave U generated in the subject 7 by the projection of the measuring light L and generating photoacoustic image data of an arbitrary cross-section, an electroacoustic transducer unit 3 which converts an acoustic signal to an electrical signal, a display unit 6 which displays the photoacoustic image data, an operation unit 5 used by an operator to enter patient information or an imaging condition of the apparatus, and a system control unit 4 which performs overall control of each unit.

The probe unit 70 of the present embodiment includes the electroacoustic transducer unit 3, diffuser plate 12, a lens system 13, optical fiber cable 14, and a light projection unit 15.

The light transmission unit 1 includes a light source unit 11 having a plurality of light sources of different wavelengths, the diffuser plate 12 which diffuses laser light Lo outputted from the light source unit 11, the lens system 13 which focuses the laser light Lo diffused by the diffuser plate 12, the optical fiber cable 14 which receives the laser light Lo focused by the lens system 13 at one end and guiding the laser light Lo, and the light projection unit 15 which projects the laser light Lo guided by the optical fiber cable 14 onto the subject 7 as the measuring light L.

The light source unit 11 includes, for example, one or more light sources which generate light of predetermined wavelengths. As for the light source, a light emitting device, such as a semiconductor laser (LD), solid-state laser, or gas-laser, which generates a particular wavelength component or monochromatic light which includes the component may be used. The light source unit 11 preferably outputs pulsed light as the laser light having a pulse width of 1 to 100 nsec. The wavelength of the laser light is determined as appropriate according to the light absorption properties of the measurement target substance within the subject. Although having a different optical absorption property depending on its state (oxygenated hemoglobin, deoxyhemoglobin, methemoglobin, carbon dioxide hemoglobin, or the like), the hemoglobin in a living body generally absorbs light having a wavelength of 600 nm to 1000 nm. Thus, if the measurement target is the hemoglobin in a living body (i.e., when imaging a blood vessel), the wavelength is preferably about 600 to 1000 nm. Further, the wavelength of the laser light is preferably 700 to 1000 nm and a wavelength in the near infrared wavelength range (about 700 to 850 nm) from the viewpoint that such light can reach a deep portion of the subject 7. The power of the laser light is preferably 10 $\mu$J/cm$^2$ to a few tens of mJ/cm$^2$ in view of the propagation losses of the laser light and photoacoustic wave, photoacoustic conversion efficiency, detection sensitivity of current detectors, and the like. The repetition of the pulse light output is 10 Hz or more from the viewpoint of image construction speed. Further, laser light may also be a pulse string in which a plurality of pulse light is arranged.

More specifically, when measuring, for example, a hemoglobin concentration in the subject 7, laser light having a pulse width of about 10 ns is formed using a Nd:YAG laser, a kind of solid-state laser, (emission wavelength: about 1000 nm) or a He—Ne gas-laser, a kind of gas-laser (emission wavelength: 633 nm). If a small light emitting device is used, such as a LD or the like, a device which uses a material, such as InGaAlP (emission wavelength: 550 to 650 nm), GaAlAs (emission wavelength: 650 to 900 nm), InGaAs or InGaAsP (emission wavelength: 900 to 2300 nm) may be used. Further, a light emitting device which uses InGaN which emits light with a wavelength not greater than 550 nm is becoming available in recent years. Still further, OPO (Optical Parametrical Oscillator) lasers which use a non-linear optical crystal capable of changing the wavelength may also be used.

The diffuser plate 12 diffuses laser light Lo outputted from the light source unit 11 and increases the beam diameter of the laser light Lo. That is, the distribution of propagation angles of luminous fluxes included in the laser beam Lo is extended by passing the laser light Lo through the diffuser plate once. This causes the light emitting face of the diffuser plate to act as the secondary light source of the laser light Lo, so that the laser light Lo is prevented from being focused too sharply when the laser light Lo is focused. The diffuser plate 12 of the present invention is preferably a light shaping diffuser. For example, the diffuser plate 12 of the present embodiment is preferably a holographic diffuser, which is a light shaping diffuser in which tiny convex lenses are arranged randomly on one surface 12s of a substrate, with a diffusion angle of 0.2 to 2.0° and more preferably with a diffusion angle of 0.4 to 1.0°. The reason is that the diffusion efficiency is high. As one of such holographic diffusers, for example, a holographic diffuser manufactured by Edmunds (Model No.: 48513-L, Material: Quartz, Diffusion angle: 0.5°, Transmission Efficiency: 93%) may be used.

Further, the light shaping diffuser may be a light shaping diffuser in which tiny concave lenses are arranged randomly on one surface of a substrate. As one of such light shaping diffusers in which tiny concave lenses are arranged, for example, a light shaping diffuser manufactured by RPC Photonics (Model No.: EDC-0.5-A, Diffusion angle: 0.5°) may be used. Further, the diffuser plate 12 of the present invention is not limited to the light shaping diffuser. Diffuser plates applicable to the present invention other than the light shaping diffuser may include diffuser plates which make use of light scattering such as, for example, a frost diffuser plate which makes use of matte effect of ground glass (sand surface) by grinding one surface of a glass substrate, an opal glass diffuser plate which makes use of the diffusion property by dispersing a milky light diffusing material in glass and the like.

As illustrated in FIG. 3, the diffuser plate 12 may be configured to be integrally held with the lens system 13 and the optical fiber cable 14 by a holding section 40a. In this case, the adjustment of positional relationship between the diffuser plate 12 and the lens system 13 becomes unnecessary and the optical system may be downsized. Preferably, the diffuser plate 12 is disposed on the upstream side of the lens system 13 in the optical system and within a range of three times the focal length of the lens system 13 from the center thereof.

The lens system 13 is provided to guide the laser light Lo to the core 41a of the optical fiber 41 of the optical fiber cable 14. The focal length (distance between the principal point on the side of the optical fiber cable 14 and focal point) of the lens system 13 is preferably 4 to 40 mm and more preferably 8 to 25 mm. The reason is that it allows downsizing of the optical system and to match the focal length with a numerical aperture NA (about 0.2 at a maximum) of general optical fibers with a silica core and a fluorine-doped silica cladding. The lens system 13 may be a coupled lens system formed of a plurality of lenses. In the case where the lens system 13 is a coupled lens system, the term "focal length of the lens system 13" refers to the combined focal length of the coupled lens system. The lens system 13 may be configured to be held integrally with the diffuser plate 12 and the optical fiber cable 14 by the holding section 40a, as illustrated in FIG. 3, or configured to be held integrally only with the optical fiber cable 14 by the holding section 40a, as illustrated in FIG. 4.

Figure 5:
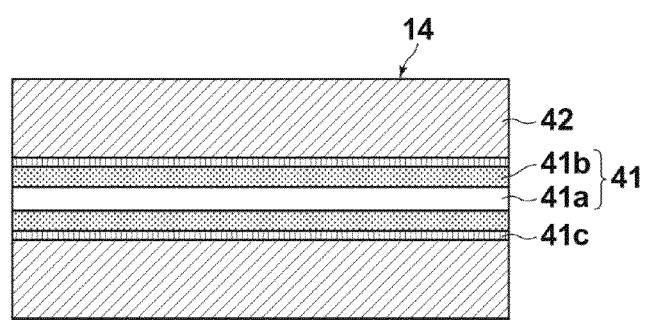
FIG. 5 is a schematic cross-sectional view of an optical fiber cable, illustrating a structure thereof.

The optical fiber cable 14 is provided to guide the laser light Lo focused by the lens system 13 to the light projection unit 15. The optical fiber cable 14 includes, for example, the optical fiber 41 formed of the core 41a and the cladding 41b, and a covering member 42, such as a ferrule, sheath, and the like, covering around the optical fiber 41, as illustrated in FIG. 5. The optical fiber 41 and the covering member 42 are fixed to each other with an adhesive 41c. The core diameter of the optical fiber 41 of the optical fiber cable 14 is preferably 100 to 600 μm and more preferably 200 to 400 μm. There is not any specific restriction on the optical fiber 41 of the optical fiber cable 14, but a silica fiber is preferable. A SMA optical fiber manufactured by Thorlabs may be used as the optical fiber cable 14.

The position of the optical fiber cable 14 is adjusted such that the input end of the optical fiber 41 is placed at the focal point of the lens system 13. In order to allow a fine positional adjustment of the optical fiber cable 14, a configuration may be adopted in which an optical fiber cable position adjustment section which moves the optical fiber cable 14 in optical axis directions is provided.

In the case where the diffuser plate 12, lens system 13, and the optical fiber cable 14 are held integrally by the holding section 40a, as illustrated in FIG. 3, or in the case where the lens system 13 and the optical fiber cable 14 are held integrally by the holding section 40b, as illustrated in FIG. 4, the optical fiber cable 14 is preferably fixed to the holding section 40a or 40b by a screw structure or the like which allows attachment to and detachment from the holding section such that the input end of the optical fiber cable 14 is fixed easily at the focal point of the lens system 13. In FIGS. 3 and 4, the optical fiber cable 14 is removably attached to the holding section 40a or 40b by providing the joint section 100a of the holding section 40a or 40b and the connection section 100b of the optical fiber cable 14 with complementary screw structures respectively. In this way, in the case where the optical fiber cable 14 is fixed to the holding section 40a or 40b by, for example, screw structures, the optical fiber cable position adjustment section becomes unnecessary and the optical system may be downsized. Further, the optical fiber cable 14 may be replaced easily by unscrewing it from the holding section 40a or 40b so that, when replacing a damaged optical fiber cable 14, the positional readjustment for the lens system 13 and the optical fiber cable 14 becomes unnecessary and the maintainability is improved. In order to integrate the lens system 13 and the optical fiber cable 14 by way of screw sections such that the positional relationship thereof is fixed, for example, the aspheric lens fiber collimation package (Model No. F280SMA-A or F280SMA-B, focal length: 18.4 mm) manufactured by Thorlabs may be used. The aspheric lens fiber collimation package series manufactured by Thorlabs provides products having focal lengths ranging from about 4 mm to 18.4 mm, so that an appropriate selection for the purpose may be made.

In the present invention, the lens system 13 focuses the laser beam Lo such that the minimum beam diameter of the laser light Lo is ⅓ to ⅔ of the core diameter of the optical fiber 41. The optical fiber 14 is preferably disposed such that the laser light Lo is inputted with the beam diameter of the laser light Lo being ⅓ to ⅔ of the core diameter of the optical fiber 41. More specifically, a divergence angle φ of the laser light Lo prior to entering the diffuser plate 12, a diffusion angle θ of the diffuser plate 12, a focal length f of the lens system 13, and a core diameter d of the optical fiber 41 preferably satisfy a formula (1) given below.

$$\frac{d}{3} \leq 2.4 \cdot f \cdot \tan\left(\sqrt{\left(\frac{\phi}{2}\right)^2 + \left(\frac{\theta}{2}\right)^2}\right) \leq \frac{2d}{3} \quad (1)$$

The reason why the beam diameter is set to ⅓ of the core diameter of the optical fiber 41 or greater is to inhibit damage of the core 41a of the optical fiber 41 (core damage mode) due to energy concentration arising from reduced beam diameter.

Figure 6:
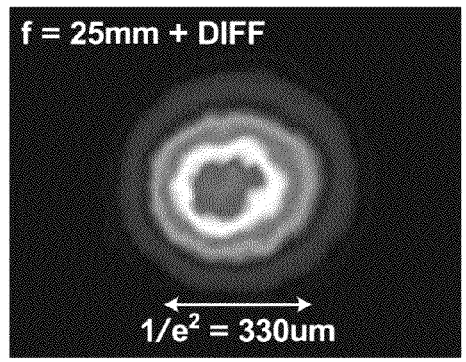
FIG. 6 illustrates a beam energy profile at the lens focus position when laser light diffused by a diffuser plate is focused by a lens system.
Figure 7:
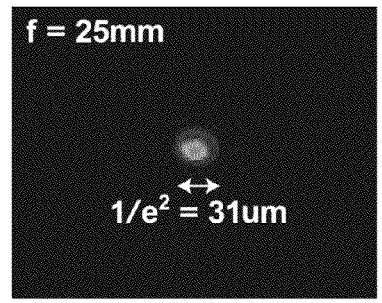
FIG. 7 illustrates a beam energy profile at the lens focus position when laser light is focused by a lens system without using the diffuser plate.

FIG. 6 illustrates a beam energy profile at the lens focus position when laser light diffused by the diffuser plate is focused by the lens system and FIG. 7 illustrates a beam energy profile at the lens focus position when laser light is focused by the lens system without using the diffuser plate. Normally, the divergence angle φ of the laser light when outputted from the laser light source is small (less than about 0.15° at most), so that the focused laser light is narrowed down to a small size at the input end of the optical fiber. As a result, the energy of the laser light is concentrated at the input end of the optical fiber and core damage occurs at the end face of the optical fiber. Consequently, in the present invention, the beam diameter of the laser light Lo at the lens focus position is controlled by diffusing the laser light Lo by the diffuser plate 12.

As the beam diameter control method, the present invention makes use of the principle that, when parallel light travelling in a direction which forms an angle α with the optical axis of a lens system enters the lens system, the position of focusing point where the parallel light is focused is displaced from the position of the focal point of the lens system, and the distance between the focusing point and the focal point can be approximated by f tan α.

Therefore, if the angle between the traveling direction of a laser light flux entering the lens system and the optical axis of the lens system has a distribution, the laser light flux is focused at a position corresponding to each angle so that the focusing range of the entire laser light formed by overlapping focusing points corresponding to the respective angles becomes large. In the case where the diffuser plate is disposed on the upstream of the lens system, the aforementioned angle distribution of the laser light flux which was about φ/2 before entering the diffuser plate is diffused within about √((φ/2)^2+ (θ/2)^2) in terms of half angle, so that the focusing range of the entire laser light focused by the lens system is further enlarged correspondingly.

Then, considering that a diameter of 1/e² in which about 86.5% of the laser light energy in the focusing range is included is taken as the beam diameter, it is presumed that the diameter of the focusing range of 2f·tan(√((φ/2)^2+(θ/2)^2)) and the beam diameter D have a certain correlation with each other.

Figure 8:
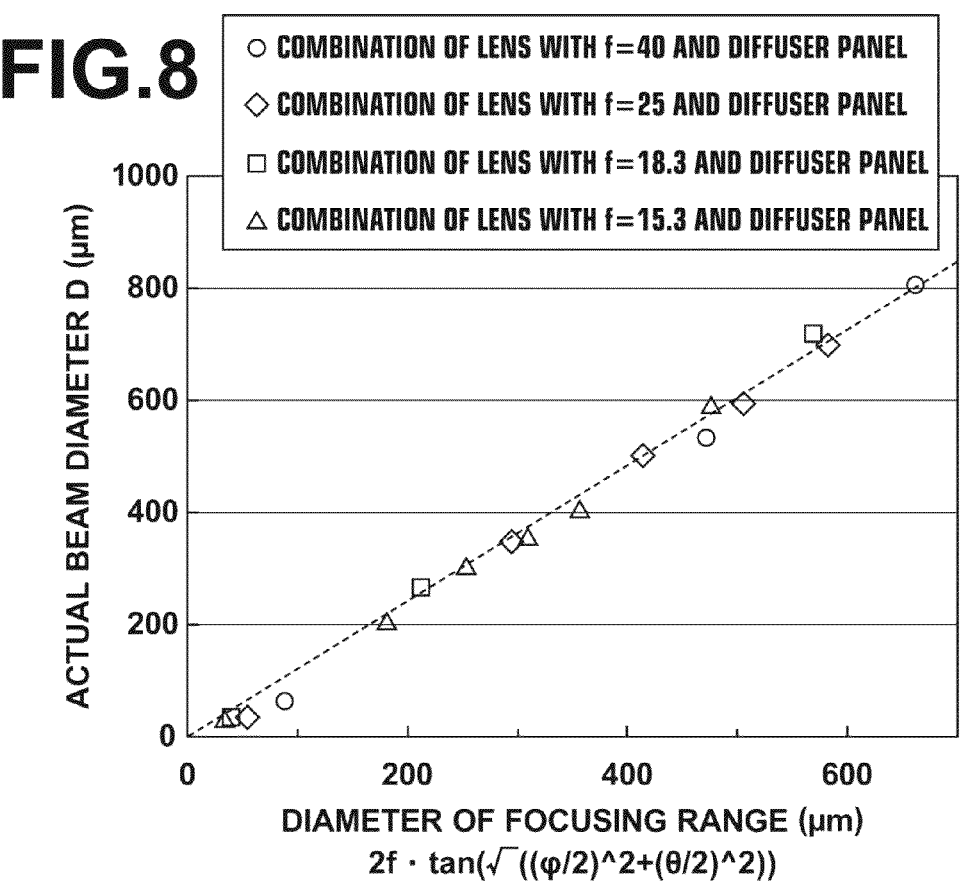
FIG. 8 is a graph illustrating a correlation between the diameter of the focusing range and the beam diameter when a laser light flux whose angle formed by the traveling direction with the axis of a lens system has a distribution is focused by the lens system.

FIG. 8 is a graph illustrating a correlation between a diameter of the focusing range 2f·tan(√((φ/2)^2+(θ/2)^2)) and an actual beam diameter D obtained by experiment when a laser light flux whose angle formed by the traveling direction with the optical axis of the lens has a distribution is focused by the lens. More specifically, the graph illustrates the results of experiment in which focusing ranges are measured by a beam profiler (LaserCam-HR manufactured by Coherent Inc.) by inputting laser light to a diffuser plate having a given diffusion angle θ, the laser light having a wavelength of 532 nm, a pulse width of 3.5 ns, a beam diameter of 3.5 mm when incident on the diffuser plate, and a divergence angle φ of 0.13°, and focusing the laser light by a lens having a given focal length f. The three circular plots in the graph illustrate the results of measurement with an optical system formed of a combination of a lens having a focal length f of 40 mm and a diffuser plate, and the diffusion angles θ of the diffuser plate are 0 (i.e., without diffuser plate), 0.65, and 0.95° respectively from the left lower plot. The five rhombic plots in the graph illustrate results of measurement with an optical system formed of a combination of a lens having a focal length f of 25 mm and a diffuser plate, and the diffusion angles θ of the diffuser plate are 0, 0.65, 0.95, 1.15, and 1.35° respectively from the left lower plot. The three rectangular plots in the graph illustrate the results of measurement with an optical system formed of a combination of a lens having a focal length f of 18.3 mm and a diffuser plate, and the diffusion angles θ of the diffuser plate are 0, 0.65, and 1.80° respectively from the left lower plot. The six triangular plots in the graph illustrate results of measurement with an optical system formed of a combination of a lens having a focal length f of 15.3 mm and a diffuser plate, and the diffusion angles θ of the diffuser plate are 0, 0.65, 0.95, 1.15, 1.35, and 1.80° respectively from the left lower plot.

It is known from FIG. 8 that the beam diameter D is in a linear functional relationship with the diameter of the focusing range. The slope of the linear function in the graph was about 2.4/2. Therefore, the beam diameter D may be represented by a formula (2) given below.

$$D = 2.4 \cdot f \cdot \tan\left(\sqrt{\left(\frac{\phi}{2}\right)^2 + \left(\frac{\theta}{2}\right)^2}\right) \quad (2)$$

That is, it can be said that any beam diameter D may be provided for a given laser light by appropriately setting the focal length f and diffusion angle θ, not limited to the focal lengths and diffusion angles used in the aforementioned experiment.

In the present invention, it is possible to guide the high energy laser light Lo through the optical fiber cable 14 without exceeding the damage threshold energy density of the core 41a of the optical fiber 41 of the optical fiber cable 14 by controlling the beam diameter D of the laser light Lo using the relationship described above.

The reason why the beam diameter is limited to ⅔ or less of the core diameter of the optical fiber 41 of the optical fiber cable 14 is that if the beam diameter D is extended, a surrounding member of the core 41a of the optical fiber 41 absorbs the energy of the laser light Lo and is damaged and emissions, such as a speck, gas, and the like, are released from the damaged region. Such emissions may adhere to the end face of the optical fiber 41 and induce damage of the core 41a near the end face, thereby causing a problem of energy transmission hindrance (ambient damage mode). That is, the reason why the beam diameter is limited to ⅔ or less of the core diameter of the optical fiber 41 is to inhibit the occurrence of the ambient damage mode described above. The term "surrounding member of the core" as used herein refers to, for example, a resin cladding, adhesive or coating covering the outer surface of the cladding, and a covering member 42, such as a metal ferrule and the like, further covering the outer circumference thereof.

Figure 9:
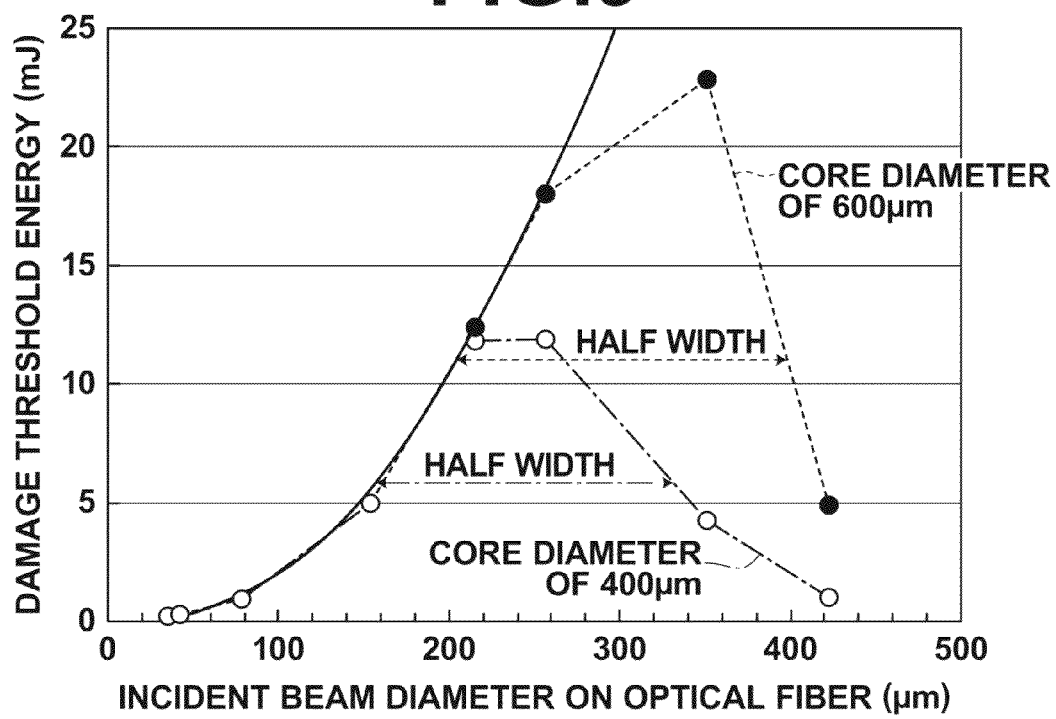
FIG. 9 is a graph illustrating the relationship between the beam diameter at the lens focus position and damage threshold energy of an optical fiber core obtained through an experiment in which conditions of the diffuser plate and the lens system were changed in various ways.

FIG. 9 is a graph illustrating the relationship between the beam diameter at the lens focus position and damage threshold energy of the optical fiber cable 14 obtained by an experiment performed by changing the conditions of the diffuser plate and the lens. More specifically, the graph plots energies when the core damage mode or ambient damage mode is started obtained by inputting laser light to a diffuser plate having a given diffusion angle θ, the laser light having a wavelength of 532 nm, a pulse width of 3.5 ns, a beam diameter of 3.5 mm when incident on the diffuser plate, and a divergence angle φ of 0.13°, and focusing the laser light on the end face of an optical fiber cable (core diameter of 600 μm or 400 μm) by a lens having a given focal length f. In the experiment, the pulse laser light described above was inputted to one end of the optical fiber and the energy of the pulse laser light outputted from the other end was measured. Then, while increasing the input energy of the pulse laser light until the input end is damaged, a maximum value of the energy measured on the output side is taken as the damage threshold energy. The beam diameter at the lens focus position is adjusted by appropriately combining a diffuser plate having a diffusion angle θ of 0.65 or 1.8° with a lens having a focal length f of 11.0, 15.3, 18.3, or 25.0 mm. In FIG. 9, the solid line illustrates a damage threshold energy curve of the end face of the optical fiber assumed from the damage threshold energy density of a silica core. The dotted line illustrates the damage threshold energy of an optical fiber cable having a silica core with a core diameter of 600 μm. Further, the dash-dot line illustrates the damage threshold energy of an optical fiber cable having a silica core with a core diameter of 400 μm. The start point of the half width corresponds to about ⅓ of the core diameter d and the end point corresponds to about ⅔ of the core diameter d.

It is known from the graph that the damage mode of the optical fiber changes from the core damage mode to the ambient damage mode in the middle of increasing in the beam diameter, and the damage threshold energy shows an upwardly convex change. This is due to the fact that the aforementioned surrounding members have low durability against the laser light Lo in comparison with the core made of silica or the like.

Further, as is known from FIG. 9, for the conventional method which focuses laser light on an optical fiber cable (600 μm core diameter) without a diffuser plate, the control range of the beam diameter is limited to about 90 μm at maximum and the amount of transferable energy is limited to about 1.0 mJ. But, the present invention in which the beam diameter D is controlled by the combination of the diffuser plate 12 and the lens system 13 allows transfer of energy such that the larger the expansion control of the beam diameter D the larger the energy amount to be transferred. For example, if the beam diameter is set to 250 μm for an optical fiber with a core diameter of 400 μm, an energy amount of about 12 mJ may be transferred and if the beam diameter is set to 350 μm for an optical fiber with a core diameter of 600 μm, an energy amount of about 22 mJ may be transferred. Thus, according to the present invention, the transferable amount of energy may be increased significantly.

The light projection unit 15 is formed of the output face of the optical fiber 41 of the optical fiber cable 14 in the present embodiment. For example, the output face of the optical fiber 41 forming the light projection unit 15 is disposed near the electroacoustic transducer unit 3. If a plurality of transducer elements 54 forming the electroacoustic transducer unit 3 is made of a transparent material, the light projection unit 15 may be disposed such that the entire transducer elements are illuminated from above the transducer elements 54.

The electroacoustic transducer unit 3 is formed of, for example, a plurality of tiny transducer elements arranged one or two dimensionally. The transducer element 54 is a piezoelectric element formed of, for example, a piezoelectric ceramic or a polymer film, such as polyvinylidene fluoride (PVDF). The electroacoustic transducer unit 3 receives a photoacoustic wave U generated in the subject 7 by the projection of light from the light projection unit 15. The transducer element 54 has a function to covert the photoacoustic wave U to an electrical signal during the reception. The electroacoustic transducer unit 3 is constructed small and light weight, and connected to a receiving unit 22 to be described later by a multi-channel cable. The electroacoustic transducer unit 3 is selected from the sector scanning type, linear scanning type, and convex scanning type according to the region of diagnosis. The electroacoustic transducer unit 3 may include an acoustic matching layer in order to efficiently transfer the photoacoustic wave U. Generally, the piezoelectric element material differs greatly from a living body in acoustic impedance and if the piezoelectric element material is brought into direct contact with the living body, the photoacoustic wave U cannot be transferred efficiently due to large reflection at the interface. Consequently, an acoustic matching layer having intermediate acoustic impedance is provided between the piezoelectric element material and the living body, whereby the photoacoustic wave U is transferred efficiently. Example materials of the acoustic matching layer include epoxy resin, silica glass, and the like.

The image generation unit 2 of the photoacoustic imaging apparatus 10 includes a receiving unit 22 which generates a receiving signal by selectively driving the plurality of transducer elements 54 forming the electroacoustic transducer unit 3 and performing in-phase addition by giving a predetermined delay time to an electrical signal from the electroacoustic transducer unit 3, a scan control unit 24 which controls the selective driving of the transducer elements 54 and delay time of the receiving unit 22, and a signal processing unit 25 which performs various kinds of processing on a receiving signal obtained from the receiving unit 22. The image generation unit 2 corresponds to an acoustic image generation unit as the signal measurement unit in the present invention.

As illustrated in FIG. 2, the receiving unit 22 includes an electronic switch 53, preamplifiers 55, receiving delay circuits 56, and an adder 57.

When receiving photoacoustic waves in the photoacoustic scanning, the electronic switch 53 sequentially selects a predetermined number of adjacent transducer elements 54. For example, if the electroacoustic transducer unit 3 is formed of 192 array type transducer elements CH 1 to CH 192, such array type transducer elements are treated by the electronic switch 53 by dividing into three areas of area 0 (area of transducer elements of CH 1 to CH 64), area 1 (area of transducer elements of CH 65 to CH 128), and area 2 (area of transducer elements of CH 129 to CH 192). In this way, the array type transducer element formed of N transducer elements is treated as a unit (area) of n (n<N) adjacent transducers and if imaging is performed with respect to each area, it is not necessary to connect the preamplifiers and A/D conversion boards to transducer elements of all of the channels, whereby the structure of the probe unit 70 may be simplified and cost increase may be prevented.

The preamplifier 55 amplifies a weak electrical signal received by the transducer element 54 selected in the manner described above to ensure a sufficient S/N.

The receiving delay circuit 56 gives a delay time to the photoacoustic wave U obtained by the transducer element 54 selected by the electronic switch 53 which matches the phases of photoacoustic waves U from a predetermined direction and forms a converged receiving beam.

The adder 57 adds up electrical signals of a plurality of channels delayed by the receiving delay circuits 56 to integrate them into one receiving signal. The acoustic signals from a given depth are in-phase added by this addition and a reception convergence point is set.

The scan control unit 24 includes a beam convergence control circuit 67 and a transducer element selection control circuit 68. The transducer element selection control circuit 68 supplies positional information of a predetermined number of transducer elements 54 to be selected by the electronic switch 53 during receiving. In the mean time, beam convergence control circuit 67 supplies delay time information for forming a reception convergence point by the predetermined number of transducer elements 54 to the receiving delay circuits 56.

The signal processing unit 25 includes a filter 66, a signal processor 59, an A/D converter 60, and an image data memory 62. The electrical signal outputted from the adder 57 of the receiving unit 22 is passed through the filter 66 to eliminate unwanted noise and a logarithmic conversion is performed on the amplitude of the received signal by the signal processor 59 to relatively emphasize a weak signal. Generally, a receiving signal from the subject 7 has amplitude with a wide dynamic range of not less than 80 dB and amplitude compression for emphasizing a weak signal is required in order to display the receiving signal on a general monitor with a dynamic range of about 23 dB. Filter 66 has bandpass characteristics with a mode in which a fundamental wave in a receiving signal is extracted and a mode in which a harmonic component is extracted. The signal processor 59 further performs envelop detection on the receiving signal subjected to the logarithmic conversion. The A/D converter 60 performs A/D conversion on the output signal from the signal processor 59 and forms photoacoustic image data of one line. The image data of one line are stored in the image data memory 62.

The image data memory 62 is a storage circuit which sequentially stores photoacoustic image data of one line generated in the manner described above. The system control unit 4 reads out data of one line for a certain cross-section stored in the image data memory 62 and required for generating a photoacoustic image of one frame. The system control unit 4 generates photoacoustic image data of one frame of the cross-section by combining the one line data while performing spatial interpolation. Then, the system control unit 4 stores the photoacoustic image data of one frame in the image data memory 62.

The display unit 6 includes a display image memory 63, a photoacoustic image data converter 64, and a monitor 65. The display image memory 63 is a buffer memory which reads out photoacoustic image data of one frame to be displayed on the monitor 65 from the image data memory 62 and temporarily stores them. The photoacoustic image data converter 64 performs D/A conversion and TV format conversion on the photoacoustic image data of one frame stored in the display image memory 63 and the output is displayed on the monitor 65.

The operation unit 5 includes a keyboard, trackball, mouse, and the like on the operation panel and used by the operator of the apparatus to input required information, such as the patient information, imaging conditions of the apparatus, cross-section to be displayed, and the like.

The system control unit 4 includes a CPU (not shown) and a storage circuit (not shown), and performs control of each unit, such as light transmission unit 1, image generation unit 2, display unit 6, and the like, in addition to overall control of the entire system according to a command signal from the operation unit 5. In particular, the internal CPU stores an input command signal from the operator via the operation unit 5.

As described above, in the photoacoustic measurement apparatus and probe unit used therewith, in particular, the measuring light (laser light) is passed through a diffuser plate once to extend the propagation angle distribution of light fluxes included in the measuring light and the beam diameter thereof at the time of entering the optical fiber is controlled by the focal length of the lens system. This may prevent the measuring light from being focused too sharply when it is focused by the lens system and inputted to the optical fiber. This may prevent the core damage mode due to local energy which exceeds the core damage threshold energy. As a result, in photoacoustic measurements performed by guiding the measuring light using an optical fiber, high energy measuring light may be guided while inhibiting end face damage of the optical fiber.

As a result, high energy measuring light can be transferred. That is, more energy can be transferred by one optical fiber cable and a stronger photoacoustic signal can be obtained. In this case, for example, a high quality photoacoustic image may be captured by the photoacoustic imaging apparatus. Further, the transmission cable of the measuring light may be reduced in size and weight, whereby the operability of the photoacoustic measurement apparatus is improved.

[Embodiment of Endoscope]

Figure 10:
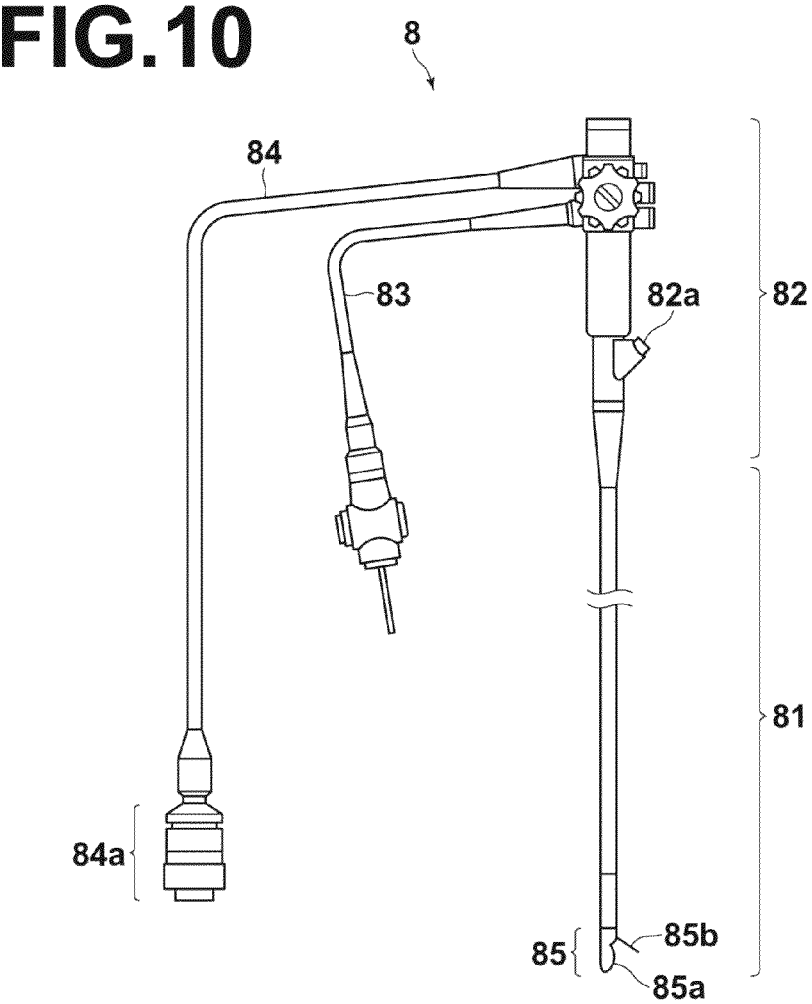
FIG. 10 is a schematic view of an embodiment of the endoscope of the present invention, illustrating a configuration thereof.
Figure 11:
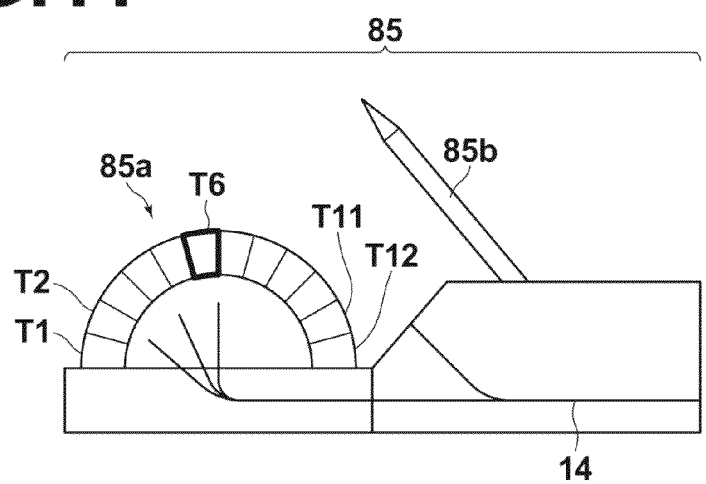
FIG. 11 is a schematic view of a tip portion of an insertion section of the endoscope of the present invention, illustrating a configuration thereof.

The probe unit of the present invention can be applied to an endoscope. FIG. 10 is a schematic view of an endoscope according to the present embodiment, illustrating the configuration thereof, and FIG. 11 is a schematic view of a tip portion of the insertion section of the endoscope of the present embodiment, illustrating the configuration thereof.

As illustrated in FIG. 10, the endoscope 8 of the present embodiment includes an insertion section 81, operation section 82, a connection code 83, and a universal code 84. In the present embodiment, the optical fiber cable 14 runs through the insertion section 81, the operation section 82, and the universal code 84 and the diffuser plate 12, the lens system 13, and the optical fiber cable 14 are integrally held, for example, at a connection section 84a on the upstream side of the universal code 84, as illustrated in FIG. 3.

The insertion section 81 of the endoscope 8 is an elongated flexible tube so as to be inserted into the body of a patient. The operation section 82 is provided at the base end of the insertion section 81 and connected to a photoacoustic measurement apparatus main body (not shown) via the connection code 83, and connected to a light source unit (not shown) and an optical observation device (not shown) via the universal code 84.

A tip portion 85 of the insertion section 81 of the endoscope 8 is provided with a convex ultrasonic transducer array 85a. Further, the optical fiber cable 14 is branched as required at the tip portion 85 of the insertion section 81 and the end portion of the branched optical fiber cable 14 is disposed such that the projection range of the laser light by the branched optical fiber cable 14 overlaps with the receiving range of the ultrasonic wave by the ultrasonic transducer array 85a. The ultrasonic transducer array 85a receives photoacoustic waves generated by the projection of laser light and outputs a plurality of receiving signals to the receiving circuit of the photoacoustic measurement apparatus main body. Further, an opening from which a puncture needle inserted from a treatment tool insertion opening 82a provided at the operation section 82 protrudes is formed at the tip portion 85 of the insertion section 81 of the endoscope 8.

As illustrated in FIG. 11, the ultrasonic transducer array 85a includes first to twelfth ultrasonic transducers TA 1 to TA 12 arranged in semi-circumference.

As described above, the endoscope of the present embodiment includes the probe unit of the present embodiment, so that the endoscope has advantageous effects identical to those described in the probe unit of the present embodiment.

[Design Changes of Probe Unit for Use with Photoacoustic Measurement Apparatus and Endoscope]

The probe unit of the present invention used, for example, with the photoacoustic measurement apparatus and endoscope is not limited to the embodiment described above.

In the probe unit of the present invention used, for example, with the photoacoustic measurement apparatus and endoscope, it is preferable to use an optical fiber cable as thin as possible with a core diameter of 100 to 600 µm since the light transmission cable portion is required to be flexible from the viewpoint of operability. Therefore, the beam diameter on the core of such an optical fiber cable is required to be 33 to 600 µm. In order to control the beam diameter within such range, the divergence angle of the laser light, diffusion angle of the diffuser plate, and the focal length of the lens system may be determined appropriately using the formula (2) given above.

The probe unit of the present invention used, for example, with the photoacoustic measurement apparatus and endoscope is required to be portable from the viewpoint that it is assumed to be moved around within a facility for use, so that the optical system is preferably downsized. If that is the case, a lens system having a relatively short focal length of 4 to 40 mm and the diffusion angle of the diffuser plate may be determined using the formula (2) given above.

In the probe unit of the present invention used, for example, with the photoacoustic measurement apparatus and endoscope, if a plurality of laser light sources is used, there may be a case in which the beam diameter entering the diffuser plate differs with respect to each light source. If the diffuser plate is a holographic diffuser plate, a large beam diameter is required in order to obtain a sufficient diffusion effect. In this case, it is preferable to adjust the diffusion angle from 0.2 to 2.0° such that the diffusion effect is obtained with a light source of the smallest beam diameter.

Figure 12:
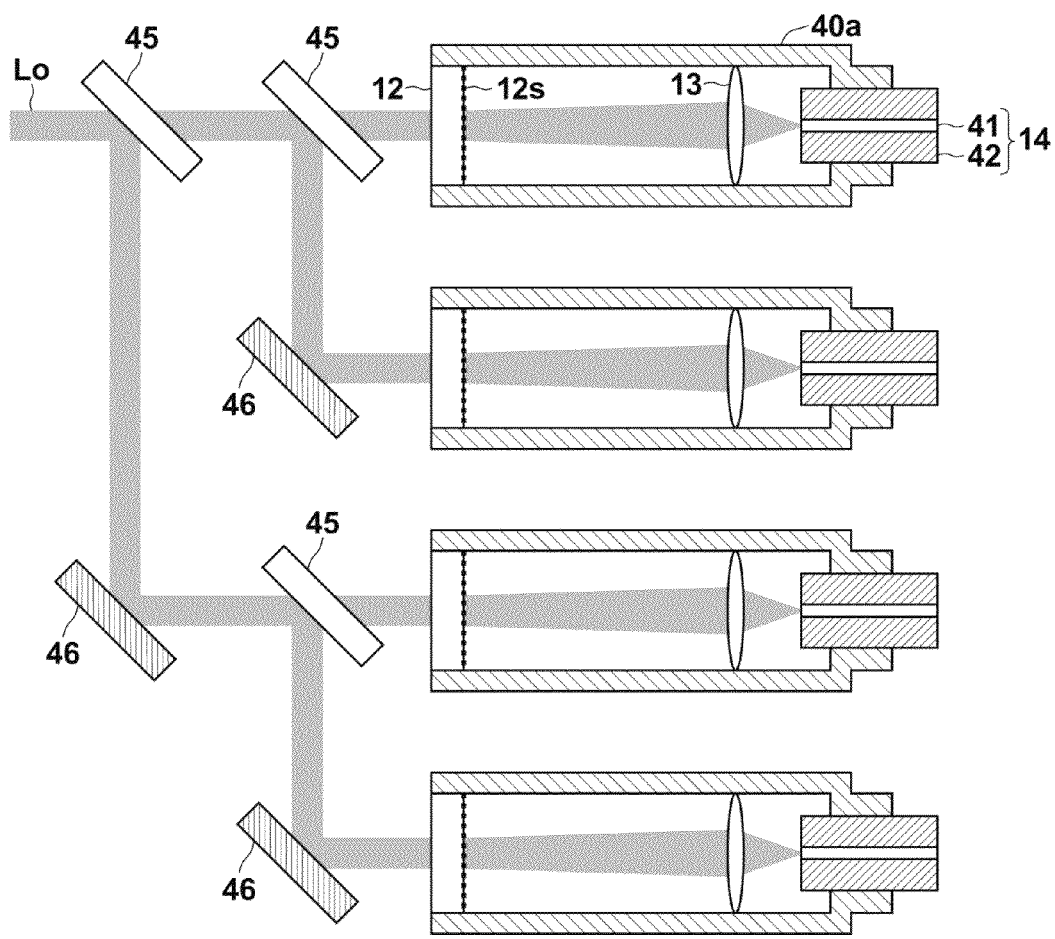
FIG. 12 is a schematic cross-sectional view of an embodiment in which an optical system formed of a diffuser plate, a lens system, and an optical fiber cable is disposed with respect to each optical path of branched laser light portions, illustrating a configuration thereof.

The probe unit of the present invention used, for example, with the photoacoustic measurement apparatus and endoscope may have a configuration in which a branch section 45, 46 which branches the laser light Lo is provided and the diffuser plate 12, the lens system 13, and the optical fiber cable 14 are integrally held by the holding section 40a and disposed with respect to each optical path of the branched laser light Lo portions, as illustrated in FIG. 12. The branch section is formed of combinations of a plurality of beam splitters 45 and a plurality of mirrors 46. The number of branches may be adjusted by the combinations of beam splitters and mirrors 46. Further, there is not any specific restriction on the number of branches, the laser light Lo is preferably branched into four or more from the viewpoint of efficient energy dispersion of the laser light Lo. This will result in that the laser light Lo is guided by a plurality of optical fiber cables 14, so that more energy can be transferred.

Figure 13:
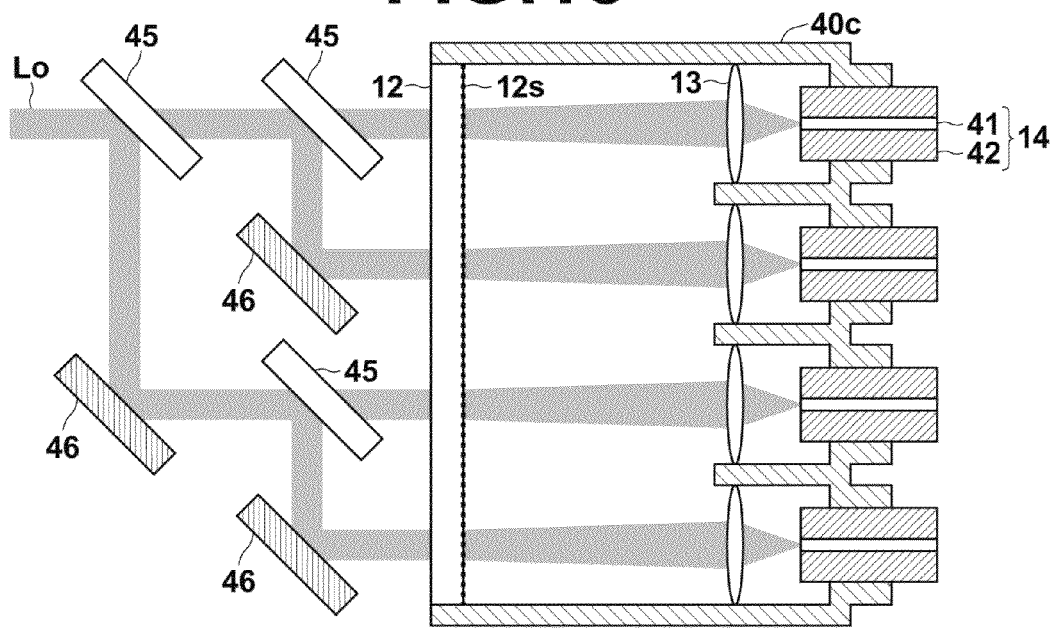
FIG. 13 is a schematic cross-sectional view of an embodiment in which an optical system formed of a lens system and an optical fiber cable is disposed for each optical path of branched laser light portions, illustrating the configuration thereof.

Further, the probe unit of the present invention used, for example with the photoacoustic measurement apparatus and endoscope of the present invention may have a configuration in which a branch section 45, 46 which branches the laser light Lo is provided, one diffuser plate 12 is disposed so as to diffuse each branched laser light Lo, and the lens system 13 and the optical fiber cable 14 are integrally held by the holding section 40c and disposed with respect to each optical path of the branched laser light Lo portions, as illustrated in FIG. 13.

The branch section is formed of combinations of a plurality of beam splitters 45 and a plurality of mirrors 46. The number of branches may be adjusted by the combinations of beam splitters and mirrors 46. Further, there is not any specific restriction on the number of branches, the laser light Lo is preferably branched into four or more from the viewpoint of efficient energy dispersion of the laser light Lo. This will result in that the laser light Lo is guided by a plurality of optical fiber cables 14, so that more energy can be transferred, as in the case described above. In addition, only one diffuser plate 12 is required, so that cost may be reduced and the optical system may be integrally accommodated in a lens barrel so that the probe unit may further be downsized.

Figure 14:
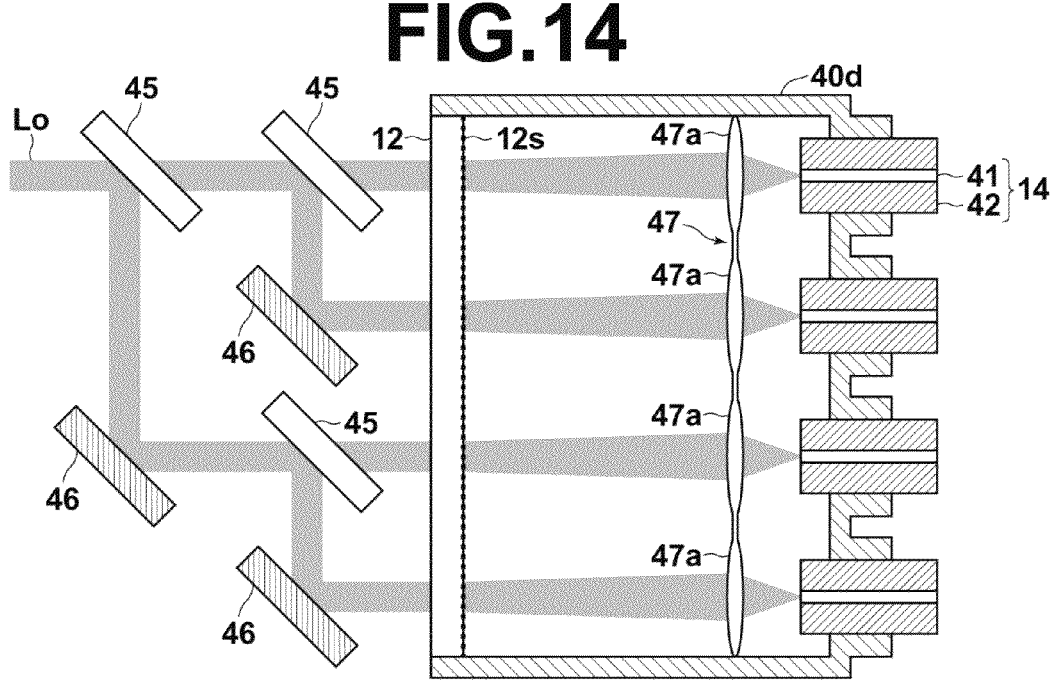
FIG. 14 is a schematic cross-sectional view of an embodiment in which an optical fiber cable is disposed with respect to each optical path of branched laser light portions using a lens array having a plurality of lens sections, illustrating a configuration thereof.

Further, the probe unit of the present invention used, for example, with the photoacoustic measurement apparatus and endoscope of the present invention may have a configuration in which the lens system is a lens array 47, a plurality of optical fiber cables 14 is provided, and the diffuser plate 12, the lens array 47, and a plurality of optical fiber cables 14 are integrated by the holding section 40d such that each end face of the plurality of optical fibers 41 of the plurality of optical fiber cables 14 on the lens array 47 side is arranged so as to correspond to each lens section 47a constituting the lens array 47, as illustrated in FIG. 14.

In this case, FIG. 14 illustrates an arrangement in which the laser light Lo is branched by the branch section constituted by combinations of beam splitters 45 and a plurality of mirrors 46 but a configuration may be adopted in which the laser light Lo is branched by the lens array 47. In this case, the lens array 47 functions as the lens system and the branch section of the present invention, and the laser light Lo diffused by the diffuser plate 12 is branched by the lens sections 47a constituting the lens array 47. In the case where the laser light Lo is branched by the lens array 47, the number of branches may be adjusted by the structure of the lens array 47. For example, in the case where a lens array formed by combining hexagonal lenses is used, the laser light may be branched into 7 or 19 branches.

Then, each laser light Lo branched by the branching function described above is focused on the core of the optical fiber 41 arranged in correspondence with each lens section 47*a* constituting the lens array 47. This will result in that the laser light Lo is guided by a plurality of optical fiber cables 14, so that more energy can be transferred as in the case described above. Further, only one diffuser plate 12 is required, so that cost may be reduced and the optical system may be integrally accommodated in a lens barrel so that the probe unit may further be downsized.

Figure 15:
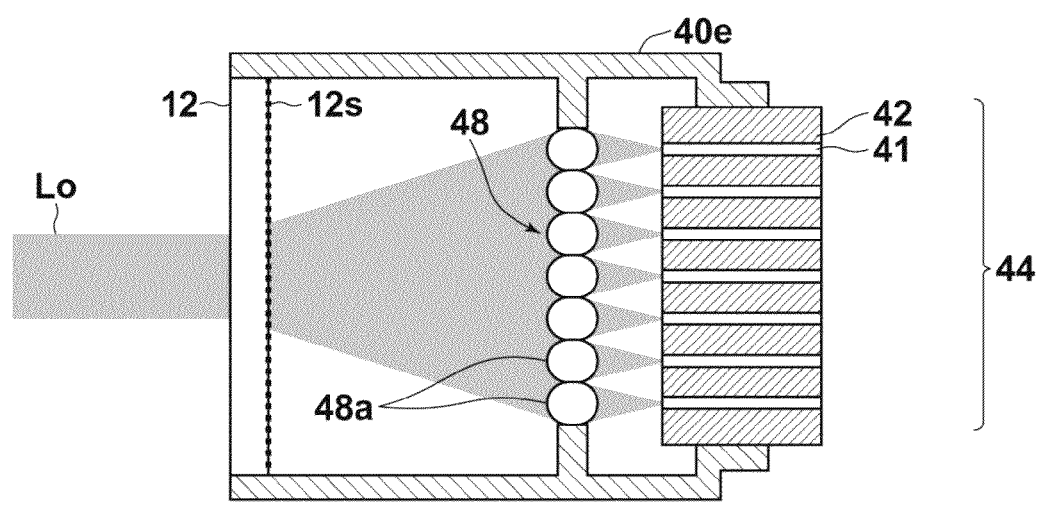
FIG. 15 is a schematic cross-sectional view of an embodiment in which laser light is branched using a micro-lens array and each of a plurality of the branched light portions is guided by a bundle fiber, illustrating a configuration thereof.

Further, the probe unit of the present invention used, for example, with the photoacoustic measurement apparatus and endoscope of the present invention may have a configuration in which the lens system is a micro-lens array 48, the optical fiber cable 14 is a bundle fiber cable 44 which includes a plurality of optical fibers 41, and the diffuser plate 12, the micro-lens array 48, and the bundle fiber cable 44 are integrated by the holding section 40*e* such that each end face of the plurality of optical fibers 41 of the bundle fiber cable 44 on the micro-lens array 48 side is arranged so as to correspond to each micro-lens 48*a* constituting the micro-lens array 48, as illustrated in FIG. 15.

In this case, the micro-lens array 48 functions as the lens system and the branch section of the present invention. The laser light Lo diffused by the diffuser plate 12 is branched by the micro-lenses 48*a* constituting the micro-lens array 48. The number of branches may be adjusted by the structure of the micro-lens array 48. There is not any specific restriction on the number of branches, the laser light Lo is preferably branched into sixteen or more from the viewpoint of efficient energy dispersion of the laser light Lo.

Each branched laser light Lo is focused on the core of the optical fiber 41 of the bundle fiber cable 44 arranged in correspondence with each micro-lens 48*a* constituting the micro-lens array 48. This will result in that the laser light Lo is guided by a plurality of optical fibers of the bundle fiber cable 44, so that more energy can be transferred, as in the aforementioned case. Further, only one diffuser plate 12 is required, so that cost may be reduced and the optical system may be integrally accommodated in a lens barrel so that the probe unit may further be downsized. Still further, the positional alignment between each of a plurality of branched light and each of a plurality of optical fibers 41 becomes easy. In addition, as the bundle fiber 44 is used, the cord portion of the probe unit may have flexibility.

Figure 16:
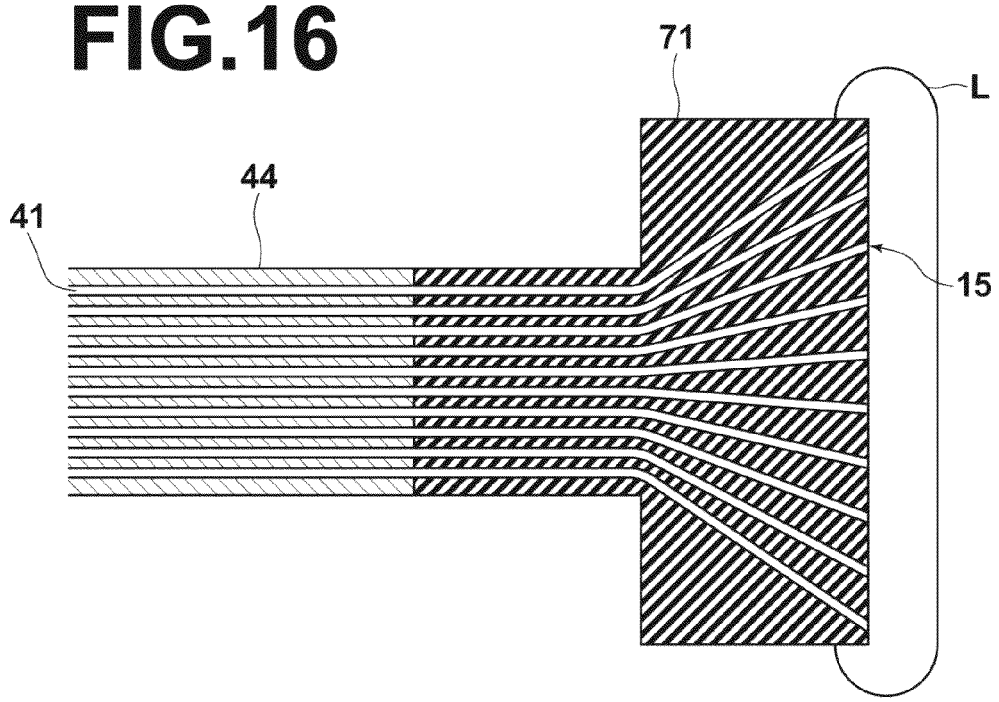
FIG. 16 is a schematic cross-sectional view of the probe unit of the present invention, illustrating a configuration of a tip portion thereof.

The probe unit used with the photoacoustic measurement apparatus of the present invention may have a configuration in which the light illumination section 15 is composed of downstream end faces of a plurality of optical fibers 41 and the end faces are arranged in a line at an interval, as illustrated in FIG. 16. Such configuration may eliminate the need to provide a complicated optical system at a tip portion 71 of the probe unit and a uniform line light source may be obtained. Further, a more uniform line light source may be obtained by adjusting the interval considering the intensity of the laser light outputted from each of a plurality of optical fibers 41. For example, the interval is preferably adjusted so as to be wide when the intensity of the laser light is high and narrow when the intensity is low.

Figure 17:
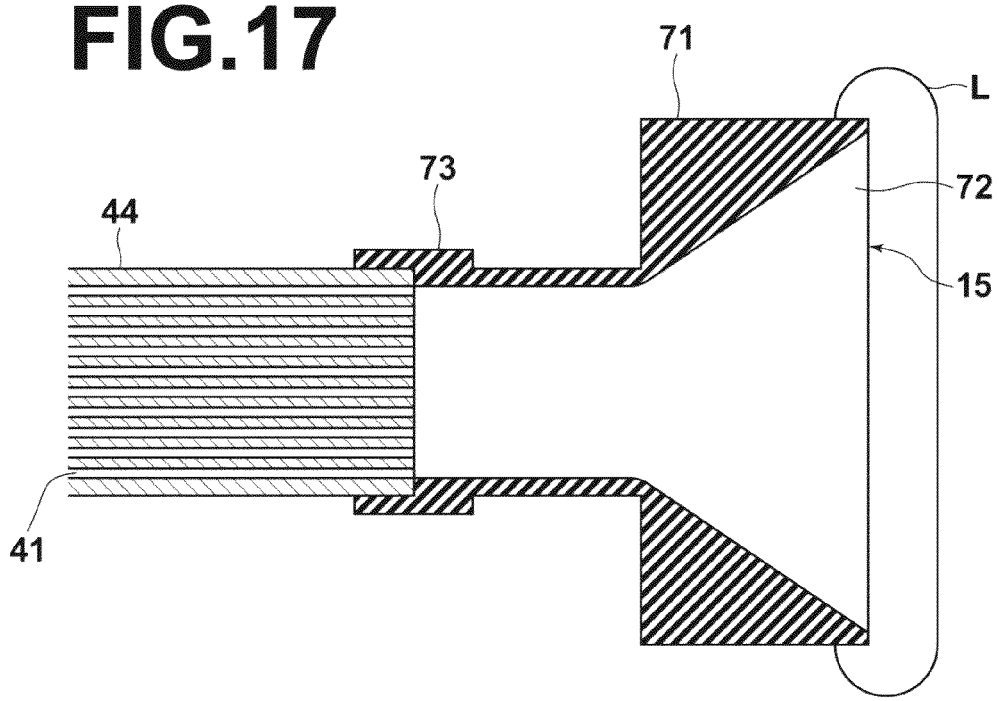
FIG. 17 is a schematic cross-sectional view of the probe unit of the present invention, illustrating another configuration of a tip portion thereof.

The probe unit used with the photoacoustic measurement apparatus of the present invention may have a configuration in which the light projection unit 15 is a club-shaped light guide plate 72 and the downstream end face of the bundle fiber cable 44 is removably connected to the short side face of the light guide plate 72, as illustrated in FIG. 17. For example, in FIG. 17, the end face of the bundle fiber cable 44 and the short side face of the light guide plate 72 are connected at the connector section 73. Such a configuration allows replacement of only the bundle fiber cable 44 when it is damaged, whereby the maintenance performance may be improved.

Further, the acoustic image generation unit may be configured to generate an ultrasonic image. In this case, the photoacoustic imaging apparatus outputs (transmits) an ultrasonic wave to a subject and detects (receive) an ultrasonic wave reflected from the subject with respect to the transmitted ultrasonic wave, in addition to detecting the photoacoustic signal described above. As for the electroacoustic transducer unit which performs the transmission and reception of ultrasonic waves, the aforementioned electroacoustic transducer unit 3 may be used or a new electroacoustic transducer unit separately provided in the probe unit 70 for the transmission and reception of ultrasonic waves may be used. Further, the transmission and reception of ultrasonic waves may be separated. For example, the ultrasonic wave may be transmitted from a position different from the probe unit 70 and the reflected ultrasonic wave with respect to the transmitted ultrasonic wave may be received by the probe unit 70.

So far the description has been made of a case in which a photoacoustic image or an ultrasonic image is generated by the photoacoustic measurement apparatus, but such image generation is not necessarily required. For example, the photoacoustic measurement apparatus may also be configured to measure the presence or non-presence of a measurement target object or a physical quantity based on the magnitude of the photoacoustic signal. Further, the measuring light is not limited to laser light.

What is claimed is:

1. A photoacoustic measurement apparatus, comprising:
   a diffuser plate which diffuses measuring light inputted from the upstream side of an optical system;
   a lens system which focuses the measuring light diffused by the diffuser plate and is disposed such that the measuring light diffused by the diffuser is inputted from the upstream side of the lens system;
   an optical fiber cable which includes an optical fiber having a core and cladding structure and is disposed such that the measuring light focused by the lens system is inputted from one end;
   a light projection unit which projects the measuring light guided by the optical fiber cable into a subject;
   an electroacoustic transducer unit which detects a photoacoustic wave generated in the subject by the projection of the measuring light and converts the photoacoustic wave into an electrical signal; and
   a signal measurement unit which performs a signal measurement based on the electrical signal.

2. The photoacoustic measurement apparatus of claim 1, wherein:
   the lens system focuses the measuring light such that a minimum beam diameter of the measuring light is ⅓ to ⅔ of a core diameter of the optical fiber; and
   the optical fiber cable is disposed such that the measuring light is inputted with a beam diameter of the measuring light being ⅓ to ⅔ of the core diameter of the optical fiber.

3. The photoacoustic measurement apparatus of claim 2, wherein a divergence angle φ of the measuring light when incident on the diffuser plate, a diffusion angle θ of the diffuser plate, a focal length f of the lens system, and a core diameter d of the optical fiber satisfy a formula (1) given below:

$$\frac{d}{3} \le 2.4 \cdot f \cdot \tan\left(\sqrt{\left(\frac{\phi}{2}\right)^2 + \left(\frac{\theta}{2}\right)^2}\right) \le \frac{2d}{3}. \quad (1)$$

4. The photoacoustic measurement apparatus of claim 1, wherein the lens system has a focal length of 4 to 40 mm.

5. The photoacoustic measurement apparatus of claim 1, wherein:
   the diffuser plate is a holographic diffuser; and
   the holographic diffuser has a diffusion angle of 0.2 to 2.0°.

6. The photoacoustic measurement apparatus of claim 1, wherein:
   the diffuser plate is a light shaping diffuser in which tiny concave lenses are arranged randomly on one surface of a substrate; and
   the light shaping diffuser has a diffusion angle of 0.2 to 2.0°.

7. The photoacoustic measurement apparatus of claim 1, wherein the optical fiber has a core diameter of 100 to 600 μm.

8. The photoacoustic measurement apparatus of claim 1, wherein the apparatus comprises a holding section which integrally holds the lens system and the optical fiber cable.

9. The photoacoustic measurement apparatus of claim 8, wherein the holding section also integrally holds the diffuser plate.

10. The photoacoustic measurement apparatus of claim 1, wherein:
    the apparatus comprises a branch section which branches the measuring light; and
    the diffuser plate, the lens system, and the optical fiber cable are disposed with respect to each optical path of the branched measuring light portions.

11. The photoacoustic measurement apparatus of claim 1, wherein:
    the apparatus comprises a branch section which branches the measuring light;
    the diffuser plate is the sole diffuser plate provided and disposed so as to diffuse at least two of the branched measuring light portions; and
    the lens system and the optical fiber cable are disposed with respect to each optical path of the branched measuring light portions.

12. The photoacoustic measurement apparatus of claim 1, wherein:
    the lens system is a lens array;
    the optical fiber cable is provided in plural; and
    each end face of the plurality of optical fibers of the plurality of optical fiber cables on the lens array side is arranged so as to correspond to each lens section constituting the lens array.

13. The photoacoustic measurement apparatus of claim 1, wherein:
    the lens system is a micro-lens array;
    the optical fiber cable is a bundle fiber cable which includes a plurality of optical fibers; and
    each end face of the plurality of optical fibers of the bundle fiber cable on the micro-lens array side is arranged so as to correspond to each micro-lens constituting the micro-lens array.

14. The photoacoustic measurement apparatus of claim 1, wherein:
    the measuring light is light in a near infrared wavelength range; and
    the diffuser plate, the lens system, and the optical fiber cable are of a structure capable of guiding light in the near infrared wavelength range.

15. The photoacoustic measurement apparatus of claim 1, wherein the signal measurement unit includes an acoustic image generation unit which generates a photoacoustic image with respect to the electrical signal of the photoacoustic wave.

16. The photoacoustic measurement apparatus of claim 15, wherein:
    the electroacoustic transducer unit detects a reflected ultrasonic wave of an ultrasonic wave transmitted to the subject;
    the acoustic image generation unit generates an ultrasonic image based on an ultrasonic wave signal of the reflected ultrasonic wave.

17. A probe unit for use with a photoacoustic measurement apparatus, comprising:
    a diffuser plate which diffuses measuring light inputted from the upstream side of an optical system;
    a lens system which focuses the measuring light diffused by the diffuser plate and is disposed such that the measuring light diffused by the diffuser is inputted from the upstream side of the lens system;
    an optical fiber cable which includes an optical fiber having a core and cladding structure and is disposed such that the measuring light focused by the lens system is inputted from one end;
    a light projection unit which projects the measuring light guided by the optical fiber cable into a subject;
    an electroacoustic transducer unit which detects a photoacoustic wave generated in the subject by the projection of the measuring light and converts the photoacoustic wave into an electrical signal; and
    a signal measurement unit which performs a signal measurement based on the electrical signal.

18. An endoscope, comprising the probe unit of claim 17.

* * * * *